United States Patent
Chang et al.

(10) Patent No.: US 9,775,577 B2
(45) Date of Patent: Oct. 3, 2017

(54) METHOD AND SYSTEM FOR DETECTION OF BONE STRUCTURE

(71) Applicant: National Applied Research Laboratories, Taipei (TW)

(72) Inventors: Wei-Jeng Chang, Taipei (TW); Chia-Yang Sun, Taipei (TW); Charlie H. Chang, Taipei (TW); Huang-Wen Huang, Taipei (TW); Po-Ying Li, Taipei (TW); Ching-I Hsieh, Taipei (TW); Cheng-Wei Ku, Taipei (TW); Kuen-Long Tasi, Taipei (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 35 days.

(21) Appl. No.: 14/947,560

(22) Filed: Nov. 20, 2015

(65) Prior Publication Data
US 2016/0302748 A1 Oct. 20, 2016

(30) Foreign Application Priority Data
Apr. 17, 2015 (TW) .............................. 104112488 A

(51) Int. Cl.
*A61B 6/00* (2006.01)
*A61B 6/03* (2006.01)
(Continued)

(52) U.S. Cl.
CPC .............. *A61B 6/505* (2013.01); *A61B 6/032* (2013.01); *A61B 6/5217* (2013.01); *G06K 9/481* (2013.01);
(Continued)

(58) Field of Classification Search
CPC .... G06K 9/4604; G06K 9/4661; G06K 9/481; G06K 2009/484; G06K 2209/055;
(Continued)

(56) References Cited

U.S. PATENT DOCUMENTS 5,673,303 A * 9/1997 Hangartner ............ A61B 6/505
378/207
5,910,972 A * 6/1999 Ohkubo .................... G06T 5/50
378/54

OTHER PUBLICATIONS

Supaporn et al. "Femur Bone Volumetric Estimation from a Single X-Ray Image for Osteoporosis Diagnosis." International Symposium on Communications and Information Technologies, Oct. 18, 2006, pp. 1149-1152.*

(Continued)

*Primary Examiner* — Jon Chang
(74) *Attorney, Agent, or Firm* — Birch, Stewart, Kolasch & Birch, LLP

(57) ABSTRACT

A method for detecting bone structure includes allocating at least one bone portion from a bone image composed by pixels each including luminance value relating to bone structural parameter; aligning a major axis of principal axes of moment of inertia of the bone portion to a principal axis of Cartesian coordinate system; a cortical bone area of the bone portion intersecting at least one principal plane perpendicular to the principal axis, and each principal plane forming an outer and inner contour line of the cortical bone area; processing an analytic algorithm for the bone structural parameter; calculating distributed state of the bone structural parameter in each principal plane to obtain a distributed state of the bone structural parameter of the bone portion; and obtaining a distributed state of the bone structural parameter of the bone portion by assembling distributed state of the bone structural parameter of each bone portion.

10 Claims, 8 Drawing Sheets

(51) Int. Cl.
*G06K 9/46* (2006.01)
*G06K 9/48* (2006.01)
*G06T 11/00* (2006.01)
*G06T 7/00* (2017.01)
*G06T 7/60* (2017.01)

(52) U.S. Cl.
CPC .............. *G06T 7/0012* (2013.01); *G06T 7/60* (2013.01); *G06K 2009/484* (2013.01); *G06K 2209/055* (2013.01); *G06T 2207/10081* (2013.01); *G06T 2207/30008* (2013.01)

(58) Field of Classification Search
CPC ..................... G06T 7/0012; G06T 7/60; G06T 2207/10081; G06T 2207/30008; A61B 6/505; A61B 6/032; A61B 6/5217
See application file for complete search history.

(56) References Cited

OTHER PUBLICATIONS

Ma et al. "Automated Image Analysis for Bone Density Measurements Using Computed Tomography." IEEE Transactions on Medical Imaging, vol. 10, No. 4, Dec. 1991, pp. 611-615.*
Sandor et al. "Spinal Bone Mineral Determination Using Automated Contour Detection—Application to Single and Dual Energy CT." Proc. SPIE 0555, Medical Imaging and Instrumentation '85, 188, Sep. 19, 1985, pp. 188-194.*

* cited by examiner

METHOD AND SYSTEM FOR DETECTION OF BONE STRUCTURE

FIELD OF THE INVENTION

The present invention relate to a method and system for bone structure detection. More specifically, the invention relates to a method and system for bone structure detection applying a particular analytic algorithm for a bone structural parameter by processing and reconstructing an image of a bone to present distributed state of the bone structural parameter of the bone.

BACKGROUND OF THE INVENTION

The prevention of osteoporosis is getting higher attention due to the health of bone and joint of elders. Osteoporosis is a major factor for judging the possibilities of being bone fracture, because the bone is fragile with osteoporosis and is easily broke after falling down accidentally. If hipbone with osteoporosis, of elder is broken, the patient only could lie on the bed and be cared by others, which not only causes huge burdens of family and society, but also causes some other diseases due to lack of exercise, muscular dystrophy, decreasing immunity etc.

Currently, ultrasonic wave and X-ray are common types to use in bone density inspection. Wherein, ultrasonic wave is aimed to inspect foot of human body. Because heel bone is the area with the highest trabecular quantity in whole body (up to 95%), the loss bone mass could be diagnosed by inspection of bone density of heel bone. However, abnormality of the heel bone mass does not actually stand for structural abnormality of other bone's mass, so bone density of lower spine and hipbone need to be inspected as well to confirm the necessity of corresponded treatments.

DEXA (Dual-energy X-ray absorptiometry) is one of X-ray type inspection approaches. Its principle of operation is using different energy level of X-ray beam to differentiate muscles and bones, and to further recognize the quantity of bone mass. The inspection approach provides X-ray to the subject to be tested, and compares the T value received by the DEXA, to the average value of young adult of the same race with peak bone mass, to show the level of bone loss. If the T value is less than −1, it means the tested subject undergoes bone loss or osteoporosis. As the result of inspection of DEXA, the T value can only stand for 4 levels (normal, low bone mass, extremely low bone mass and osteoporosis), which is not including specified state of each position of the bone.

Therefore, in the field of treatments for osteoporosis, a method and system is needed to calculate and analyze distributed state of bone structural parameter of bone, distributed state of bone structural parameter with 3D graphic, according to operation process and image reconstruction, which is beneficial to orthopedist or related researcher.

SUMMARY OF THE INVENTION

Accordingly, the present invention provides a method and system for detection of bone structure, which executes operation process and image reconstruction according to an image of a bone captured by CT (computerized tomography) scanner, to present distributed state of bone structural parameter of the bone for diagnosing osteoporosis, and to discover and prevent bone being more fragile and easier to fracture.

The present invention relates to a method for detection of bone structure, which comprises: (1) allocating at least one bone portion from an image of a bone to be analyzed, wherein the image of the bone portion is composed by pixels, and each pixel includes luminance value positively relating to a bone structural parameter (e.g., bone density); (2) aligning a major axis of principal axes of moment of inertia of the bone portion to a principal axis of Cartesian coordinate system; (3) a cortical bone area of the bone portion intersecting at least one principal plane which is perpendicular to the principal axis, and each principal plane forming an outer contour line and an inner contour line of the cortical bone area; (4) processing a analytic algorithm for the bone structural parameter, in the inner area of the outer contour line in the principal plane, to obtain a distributed state of the bone structural parameter along the outer contour line; (5) calculating distributed state of the bone structural parameter along the outer contour line in each principal plane, to obtain a distributed state of the bone structural parameter of the bone portion; (6) and assembling distributed state of the bone structural parameter of each bone portion, to obtain a distributed state of the bone structural parameter of the bone.

In one embodiment of the present invention, the bone structural parameter is bone density and the analytic algorithm for bone density is a normal vector algorithm calculating normal vector of the pixel of the outer contour line in the principal plane, cumulating, from the pixel to the inner area of the outer contour line along normal vector, luminance value of each pixel of the area between the outer contour line and the inner contour line and calculating distance between the outer contour line and the inner contour line along normal vector, to obtain a distributed state of bone density of each pixel of the outer contour line after foresaid calculation of each pixel.

In another embodiment of the present invention, the bone structural parameter is bone density and the analytic algorithm for bone density is a depth algorithm calculating a center position of the area between the outer contour line and the inner contour line in the principal plane, forming connecting lines separately from the center position to each pixel of the outer contour line, cumulating luminance value of each pixel over each connecting line and calculating distance between the outer contour line and the inner contour line.

In another embodiment of the present invention, the bone structural parameter is bone density and the analytic algorithm for bone density is a ring algorithm calculating a center position of the area between the outer contour line and the inner contour line in the principal plane, forming radial lines with fixed separation angle each, outward to reach the outer contour line, cumulating luminance value of each pixel over each radial line and calculating distance between the outer contour line and the inner contour line.

In another embodiment of the present invention, the radial lines of the ring algorithm are with variant separation angle each.

In another embodiment of the present invention, the foresaid method obtains a distributed state of the bone structural parameter along the outer contour line with 3D Geographic Positioning System Map, according to the calculation of the analytic algorithm for the bone structural parameter.

In another embodiment of the present invention, the foresaid method obtains a distributed state of the bone structural parameter along the outer contour line with 3D Visualization, according to the calculation of the analytic algorithm for the bone structural parameter.

In another embodiment of the present invention, the foresaid method obtains a distributed state of the bone structural parameter along the outer contour line with 2D Map, according to the calculation of the analytic algorithm for the bone structural parameter.

In another embodiment of the present invention, in the 3D Geographic Positioning System Map, the length and width present position of each pixel corresponding to the bone portion, and the height presents the bone structural parameter of each pixel.

In another embodiment of the present invention, in the 2D Map, the length and the width present position of each pixel corresponding to the bone portion, and the color distribution presents the bone structural parameter of each pixel.

The present invention relates to a system for detection of bone structure, which comprises: a CT unit, an image process unit, a bone structural parameter calculation unit and a display unit. Wherein, the CT unit includes a X-ray transmitter and a receiver and transmits X-ray through a tested organism between the X-ray transmitter and the receiver; the image processor unit transforms X-ray beam received by the receiver, to an image; a bone structural parameter calculation unit includes the foresaid method for detection of bone structure, executing operation process and image reconstruction according to the image of the bone processed by the CT unit and the image process unit to present distributed state of the bone structural parameter of the bone; and a display unit displays distributed state of the bone structural parameter of the bone calculated by the bone structural parameter calculation unit.

The description of the present invention has been presented for purposes of illustration and description, and many modifications and variations will be apparent to those of ordinary skill in the art without departing from the scope and spirit of the invention. Therefore, the following embodiments was chosen and described in order to best explain the principles of the invention and the practical application but not intended to be exhaustive or limited to the invention in the form disclosed.

DETAILED DESCRIPTION OF THE INVENTION

If not otherwise defined, all terms (including technical and scientific terms) have the same meaning as those of ordinary skill in the art understand.

As used herein, unless the context clearly dictates otherwise, the singular forms "a", "an" and "the present" include the plural forms (at least one).

In one aspect, the present invention provides a method for detection of bone structure, which executes operation process and image reconstruction according to an image of a bone captured by CT scanner to present distributed state of bone structural parameter of the bone, for diagnosing osteoporosis to discover and prevent bone being more fragile and easier to fracture.

Figure 1:
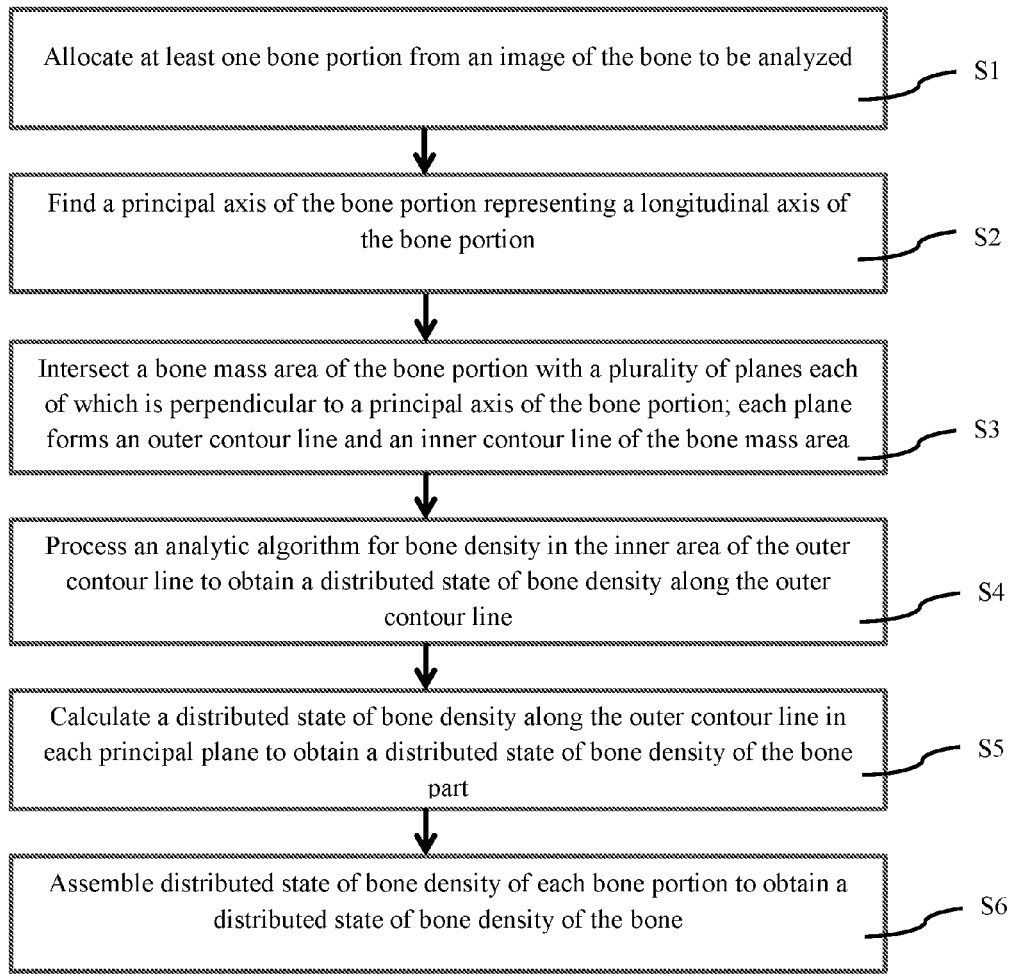
FIG. 1 illustrates a flow chart of the method for detecting bone structure according to the present invention.
Figure 2:
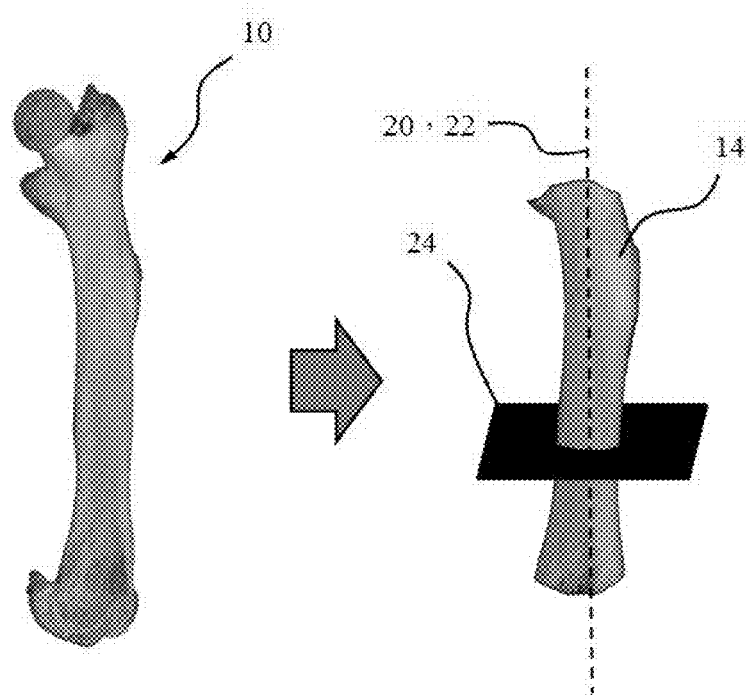
FIG. 2 illustrates a tested bone of one embodiment of the method for detecting bone structure according to the present invention.

According to the statement from International Osteoporosis Foundation, about 12% to 20% elder patients were dead within a year after their hipbone fracturing. Therefore, embodiments of the present invention analyze thighbone and calculate distributed state of a bone structural parameter to prevent the hipbone fracturing. FIG. 1 illustrates a flow chart of the method for detecting bone structure according to the present invention, and FIG. 2 illustrates a tested bone of one embodiment of the method for detecting bone structure according to the present invention. Referring to FIG. 1 and FIG. 2, the bone structural parameter is bone density. After the tested one is scanned by the CT scanner, a captured image have been processed and reconstructed by computer to obtain three dimensional images of human tissue and structure. In the method for detection of bone structure of the present invention, the first step (51) allocates a bone (10) in an irregular shape, to at least one bone portion (14) and analyzes each bone portion (14). An image of the bone portion (14) is composed by pixels (16), and each pixel (16) includes luminance value positively relating to a bone structural parameter (e.g., bone density). The second step (S2) is aligning a major axis (20) of principal axes of moment of inertia of the bone portion (14) to a principal axis (22) of Cartesian coordinate system. The third step (S3) is intersecting a bone mass area of the bone portion (14) with at least one principal plane (24), wherein each principal plane (24) forms an outer contour line (26) and an inner contour line (28) of a cortical bone area. The forth step (S4) is processing an analytic algorithm (30) for bone density, in the inner area of the outer contour line (26) in the principal plane (24), to calculate distributed state of bone density along the outer contour line (26). The fifth step (S5) is calculating distributed state of bone density along the outer contour line (26) in each principal plane (24), to obtain a distributed state of bone density of the bone portion (14). The sixth step (S6) is assembling distributed state of bone density of each bone portion (14), to obtain a distributed state of bone density of the bone (10).

The bone (10) is composed by bone portion (14) in irregular shape, and two ends of the bone (10) include more complicated structure. The bone (10) is allocated to various areas suitable for being analyzed (shown in FIG. 2). Firstly, allocate the middle part, which is in more regular shape, of the bone (10), and calculate to find out the major axis (20) of principal axes of moment of inertia of bone portion (14) after being allocated, in order to rotate the major axis vector of the major axis (20) of principal axes of moment of inertia to align with the principal axis (22) (e.g., Z-axis) of Cartesian coordinate system. The cross section of the bone portion (14) is performed in at least one principal plane (24) (e.g., X-Y plane) which is perpendicular to the principal axis (22), by the foresaid step. In part of embodiments of the present invention, two ends or other parts of the bone (10), with more complicated structure, can be allocated to several bone portions in more regular shape, and foresaid step can be used to rotate the major axis vector of the major axis of principal axes of moment of inertia to align with the principal axis of Cartesian coordinate system, in which the distributed state of bone density of the bone portions can be individually figured out by a analytic algorithm (30) for bone density.

Additionally, in the method for detection of bone structure according to the present invention, the unit of luminance value of each pixel (16) in the image of the bone (10) captured by the CT scanner, is Hounsfield unit (HU) varying to reflect different level of organs' absorption of X-ray, and area with high value of Hu indicates that the absorption is high as a high density area, like bones. As the value of (HU) gets higher, the luminance of the image will become higher, and the density of the bone portion can be analyzed by the image according to this relationship.

In the method for detection of bone structure according to the present invention, three different kinds of analytic algorithm (30) for bone density are applied to calculate and analyze inner area of the outer contour line (26) in the principle plane (24), wherein the area between the outer contour line (26) and an inner contour line (28) is formed in each principle plane, the area corresponding to a cortical bone area of the bone portion (14).

Figure 3:
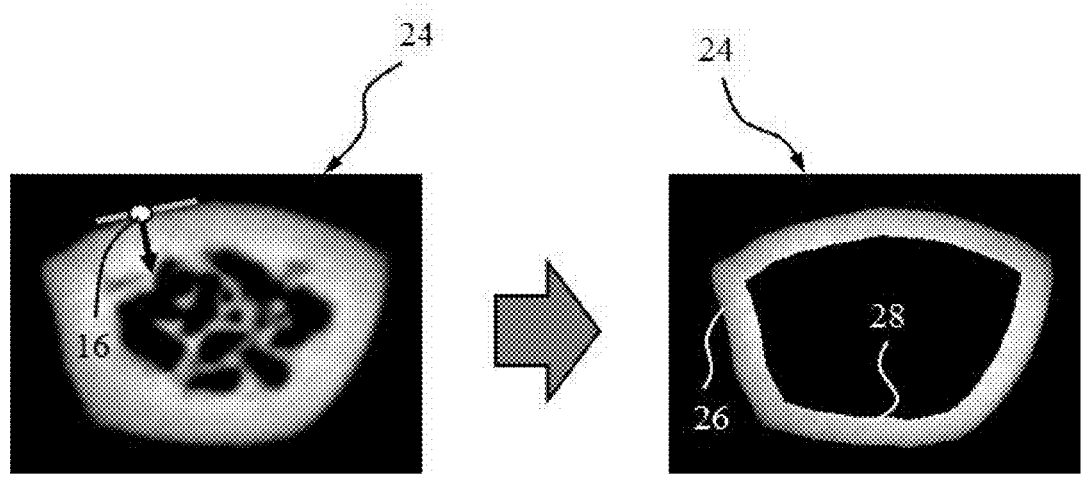
FIG. 3 illustrates a normal vector algorithm of the method for detecting bone structure according to the present invention.

The first type of analytic algorithm (30) for bone density is a normal vector algorithm (40) (referring to FIG. 3) cumulating, from each pixel (16) of the outer contour line (26) to the center of the bone portion along normal vector of each pixel (16), luminance value of the area between the outer contour line (26) and the inner contour line (28), in each principal plane (24), and calculating bone plate thickness in the area between the outer contour line and the inner contour line. Calculate tangent vector of the pixel (16) before calculating normal vector of each pixel (16) of the outer contour line (26), and then the normal vector can be obtained by rotating the tangent vector with 90 degree.

Figure 4:
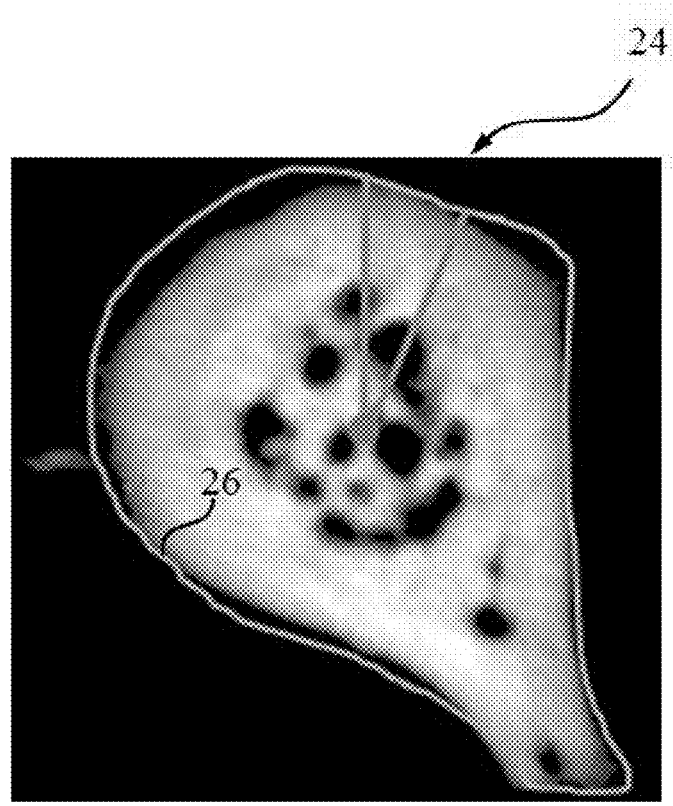
FIG. 4 illustrates a depth algorithm of the method for detecting bone structure according to the present invention.

The second type of analytic algorithm (30) for bone density is a depth algorithm (50) (referring to FIG. 4) calculating a center position of the area between the outer contour line (26) and the inner contour line (28) in each principal plane (24), forming connecting lines from the center position to each pixel (16) of the outer contour line (26) in the principal plane (24), cumulating luminance value of each connecting line and calculating bone plate thickness in the area between the outer contour line (26) and the inner contour line (28), to obtain the bone analysis result of the principal plane (24). Applying the foresaid step repeatedly to each principal plane (24) can result the analysis of the whole bone portion.

Figure 5:
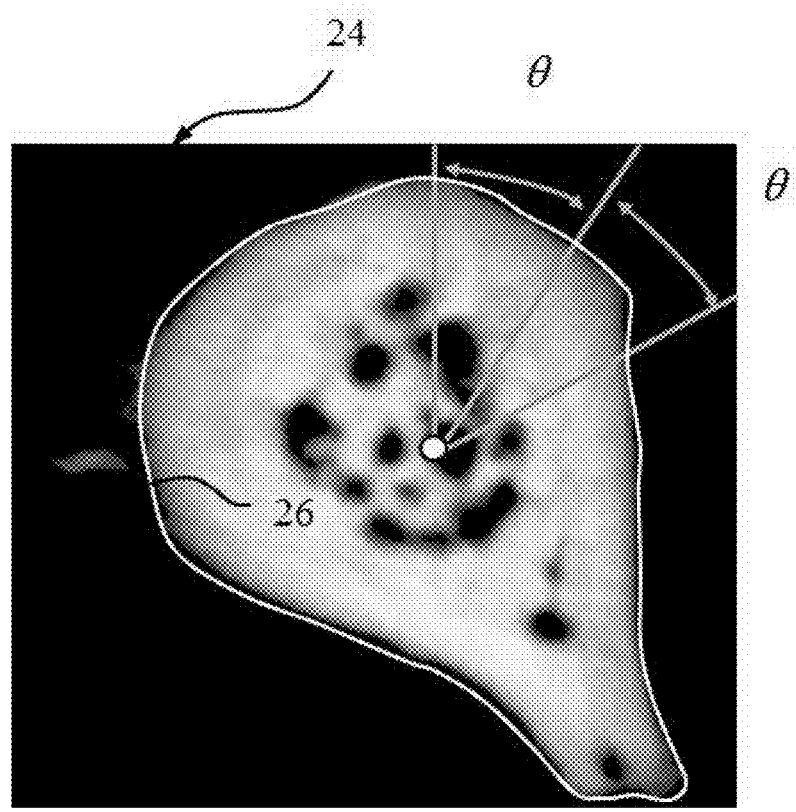
FIG. 5 illustrates a ring algorithm of the method for detecting bone structure according to the present invention.

The third type of analytic algorithm (30) for bone density is a ring algorithm (60) (referring to FIG. 5) calculating a center position of the area between the outer contour line (26) and the inner contour line (28) in each principal plane (24), and forming scan lines from the center position, radiating around 360 degree outward and stepping by each pixel (16) to reach the outer contour line (26). Cumulate luminance value over each radial line to obtain the bone analysis result of the principal plane (24), and apply the foresaid step repeatedly to each principal plane (24) can result the analysis of the whole bone. The angle between radial lines can be fixed (e.g., 1 degree) or be various, which is not limited in the present invention.

Figure 6:
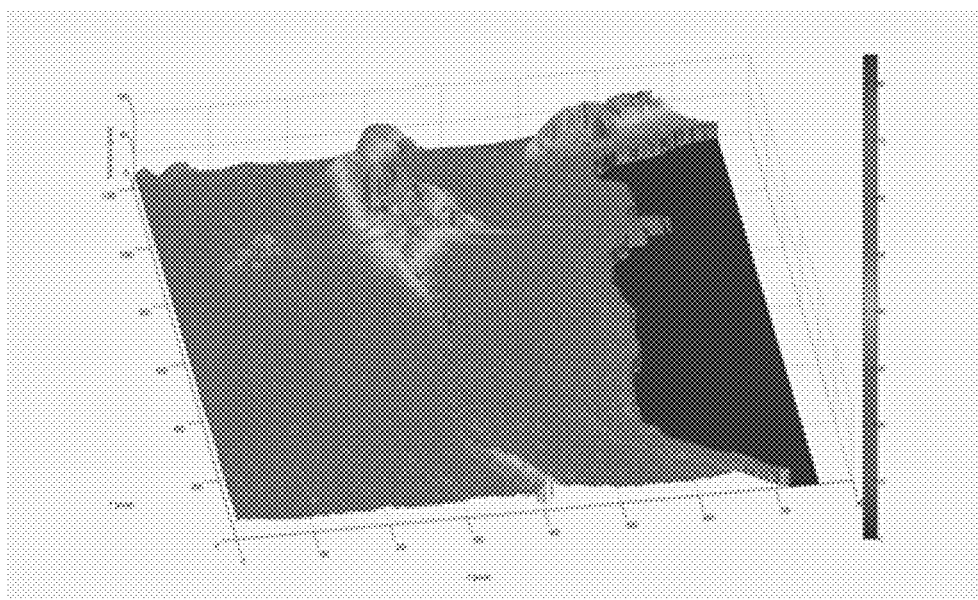
FIG. 6 illustrates a 3D Geographic Positioning System Map of the method for detecting bone structure according to the present invention.
Figure 7:
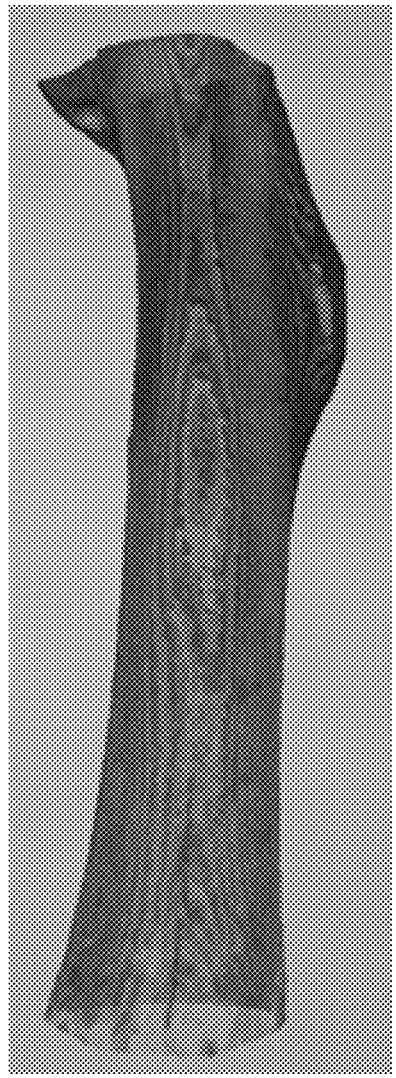
FIG. 7 illustrates a 3D Visualization of the method for detecting bone structure according to the present invention.
Figure 8:
FIG. 8 illustrates a 2D Map of the method for detecting bone structure according to the present invention.

Calculating the inner area of the outer contour line (26) in each principal plane (24) by foresaid three different types of analytic algorithm (30) for bone density, could obtain the cumulated luminance value (HU) corresponding to each pixel (16) over the outer contour line (26) (outer surface of the cortical bone area) of the bone portion (14). Furthermore, the method for detection of bone structure of the present invention executes operation process and image reconstruction to present the foresaid result with 3D Geographic Positioning System Map, 3D Visualization or 2D Map (referring FIG. 6, FIG. 7 and FIG. 8), wherein, in 3D Geographic Positioning System Map, the length and width present position of each pixel corresponding to the bone portion and the height presents the bone structural parameter of each pixel. Additionally, different amounts of cumulated luminance value corresponding to each pixel 16 is presented by different colors, and distribution of colors in 3D Visualization and 2D Map could be used to diagnose osteoporosis by orthopedist or related researcher.

Another part of the present invention provides a system for detection of bone structure, the system comprising a CT unit, an image process unit, a bone structural parameter calculation unit and a display unit. The CT unit includes a X-ray transmitter and a receiver, transmitting X-ray through a tested organism between the X-ray transmitter and the receiver; the image process unit transforms X-ray beam received by the receiver, to an image; the bone structural parameter calculation unit includes the foresaid method for detection of bone structure, executing operation process and image reconstruction according to the image of the bone (10) processed by the CT unit and the image process unit to present distributed state of a bone structural parameter of the bone (10); and the display unit displays distributed state of the bone structural parameter of the bone (10) calculated by the bone structural parameter calculation unit.

In the system for detection of bone structure according to the present invention, the bone structural parameter is bone density, and the bone structural parameter calculation unit includes three kinds of analytic algorithm (30) for bone structural parameter, which are a normal vector algorithm (40), a depth algorithm (50) and a ring algorithm (60). The normal vector algorithm (40) calculates normal vector of the pixel (16) of the outer contour line (26) in each principal plane (24), cumulates, from the pixel (16) to the inner area of the outer contour line (26) along normal vector, luminance value of the area between the outer contour line (26) and the inner contour line (28), and calculates the distance along normal vector between the outer contour line (26) and the inner contour line (28), to obtain distributed state of bone density of each pixel (16) over the outer contour line (26); the depth algorithm (50) calculates a center position of the area between the outer contour line (26) and the inner contour line (28) in each principal plane (24), forms connecting lines separately from the center position to each pixel (16) of the outer contour line (26), cumulates luminance value of each pixel (16) over each connecting line and calculates distance between the outer contour line (26) and the inner contour line (28); and the ring algorithm (60) calculates a center position of the area between the outer contour line (26) and the inner contour line (28) in each principal plane (24), forms radial lines outward to reach the outer contour line (26), cumulates luminance value of each pixel (16) over each radial line, and calculates distance between the outer contour line (26) and the inner contour line (28), wherein the angle between radial lines can be fixed or various.

In the system for detection of bone structure of the present invention, the result after calculating and analyzing the inner area of the outer contour line (26) in each principal plane

(24) by three different types of analytic algorithm (30) for bone density, could be presented with 3D Geographic Positioning System Map, 3D Visualization or 2D Map.

As mentioned above, the method and system for detection of bone structure according to the present invention figures out distributed state of the bone (10) by three types of analytic algorithm (30) (the normal vector algorithm (40), the depth algorithm (50) and the ring algorithm (60)) and performs it with 3D Geographic Positioning System Map, 3D Visualization or 2D Map. The actual application of embodiments of the present invention is effective to discover the variant which could be compared to half year before or after, of distributed state of bone structure parameter of the patient, and effective to figure out the variant position of bone structure parameter. Therefore, the method and system for detection of bone structure of the present invention is actually available to calculate and analyze distributed state of bone structure parameter of the bone, which is not only beneficial to research by orthopedist or related researcher, but also prevents disease like bone fracture of elders, caused by osteoporosis.

Those of ordinary skill in the art can understand invention various modifications and alternative forms, the example shows by figure and here a detailed description of specific embodiments. Therefore, induction detailed description, it should be limited to any disclosed particular embodiments, but should cover all the variations and modifications are included within the scope of the present invention, as set forth in the following claims.

What is claimed is:

1. A method for detection of bone structure, executing operation process and image reconstruction of an image of a bone captured by CT scanner to present distributed state of bone density of the bone for diagnosing osteoporosis, the bone including a plurality of bone portions, the method comprising:
    allocating one bone portion of the plurality of bone portions from the image of the bone to be analyzed, wherein the image of the one bone portion is composed by pixels, and each pixel includes a luminance value positively relating to a bone structural parameter;
    finding a principal axis of the one bone portion representing a longitudinal axis of the one bone portion;
    intersecting a bone mass area of the one bone portion with a plurality of planes each of which is perpendicular to the principal axis of the one bone portion, such that an outer contour line and an inner contour line of the bone mass area are formed on each of the plurality of planes;
    processing an analytic algorithm for the bone structural parameter, in an inner area of the outer contour line on each of the plurality of planes, to obtain a respective distributed state of the bone structural parameter along the respective outer contour line;
    repeating the foregoing steps to obtain a plurality of distributed states of the bone structural parameter of the plurality of bone portions;
    assembling said plurality of distributed states of the bone structural parameter of the plurality of bone portions, to obtain a distributed state of the bone structural parameter of the bone.

2. The method according to claim 1, wherein the bone structural parameter is bone density.

3. The method according to claim 2, wherein the analytic algorithm for bone density is a normal vector algorithm calculating a normal vector of the pixel of the outer contour line on each of the plurality of planes, cumulating, from the pixel to the inner area of the outer contour line along the normal vector, the luminance value of each pixel of the area between the outer contour line and the inner contour line and calculating distance between the outer contour line and the inner contour line along the normal vector, to obtain a distributed state of bone density of each pixel of the outer contour line after foresaid calculation of each pixel.

4. The method according to claim 2, wherein the analytic algorithm for bone density is a depth algorithm calculating a center position of the area between the outer contour line and the inner contour line on each of the plurality of planes, forming connecting lines separately from the center position to each pixel of the outer contour line, cumulating the luminance value of each pixel over each connecting line and calculating distance between the outer contour line and the inner contour line.

5. The method according to claim 2, wherein the analytic algorithm for the bone density is a ring algorithm calculating a center position of the area between the outer contour line and the inner contour line on each of the plurality of planes, forming radial lines with fixed separation angle each, outward to reach the outer contour line, cumulating luminance value of each pixel over each radial line and calculating distance between the outer contour line and the inner contour line.

6. The method according to claim 2, comprising obtaining the plurality of distributed states of the bone density along the respective outer contour lines with a 3D Geographic Positioning System Map, according to the calculation of the analytic algorithm for bone density.

7. The method according to claim 6, wherein, in the 3D Geographic Positioning System Map, both a length and a width represent a position of each pixel corresponding to the bone portion, and a height represents the bone structural parameter of each pixel.

8. The method according to claim 2, comprising obtaining the plurality of distributed states of the bone density along the respective outer contour lines with a 3D Visualization, according to the calculation of the analytic algorithm for bone density.

9. The method according to claim 2, comprising obtaining the plurality of distributed states of the bone density along the respective outer contour lines with a 2D Map, according to the calculation of the analytic algorithm for bone density.

10. The method according to claim 9, wherein, in the 2D Map, both a length and a width represent a position of each pixel corresponding to the bone portion, and a color distribution represents the bone structural parameter of each pixel.

* * * * *